(12) United States Patent
Pomedli

(10) Patent No.: US 10,820,474 B2
(45) Date of Patent: Nov. 3, 2020

(54) SYSTEM FOR ESTIMATING FIELD CONDITIONS AND ASSOCIATED METHODS FOR ADJUSTING OPERATING PARAMETERS OF AN AGRICULTURAL MACHINE BASED ON ESTIMATED FIELD CONDITIONS

(71) Applicant: CNH Industrial Canada, Ltd., Saskatoon (CA)

(72) Inventor: Barry M. Pomedli, Saskatoon (CA)

(73) Assignee: CNH Industrial Canada, Ltd., Saskatoon, Saskatchewan (CA)

( * ) Notice: Subject to any disclaimer, the term of this patent is extended or adjusted under 35 U.S.C. 154(b) by 167 days.

(21) Appl. No.: 16/157,593

(22) Filed: Oct. 11, 2018

(65) Prior Publication Data
US 2020/0113122 A1 Apr. 16, 2020

(51) Int. Cl.
| | |
|---|---|
| *A01B 76/00* | (2006.01) |
| *A01B 63/00* | (2006.01) |
| *A01B 69/04* | (2006.01) |
| *A01B 69/00* | (2006.01) |
| *G01N 33/24* | (2006.01) |
| *G01N 21/84* | (2006.01) |
| *G06K 9/00* | (2006.01) |
| *A01B 79/00* | (2006.01) |

(52) U.S. Cl.
CPC ............ *A01B 76/00* (2013.01); *A01B 63/008* (2013.01); *A01B 69/001* (2013.01); *A01B 69/008* (2013.01); *A01B 79/005* (2013.01); *G01N 21/84* (2013.01); *G01N 33/24* (2013.01); *G06K 9/0063* (2013.01); *G01N 2033/245* (2013.01)

(58) Field of Classification Search
None
See application file for complete search history.

(56) References Cited

U.S. PATENT DOCUMENTS

| | | |
|---|---|---|
| 3,197,733 A | 7/1965 | Cowie |
| 6,630,885 B2 | 10/2003 | Hardman et al. |
| 7,082,819 B2 | 8/2006 | Thiesen et al. |
| 7,295,103 B2 | 11/2007 | Muller et al. |

(Continued)

FOREIGN PATENT DOCUMENTS

| | | | |
|---|---|---|---|
| CN | 102303488 A | 1/2012 | |
| DE | 102011001858 A1 * | 10/2012 | ........... A01D 41/127 |
| WO | WO 96/10727 A1 | 4/1996 | |

OTHER PUBLICATIONS

Translation of DE 10 2011 001 858 A1, Behnke, 23 pages (Year: 2011).*

*Primary Examiner* — Dale W Hilgendorf
*Assistant Examiner* — Alexander C. Bost
(74) *Attorney, Agent, or Firm* — Rickard K. DeMille; Rebecca L. Henkel

(57) ABSTRACT

In one aspect, a system for estimating field conditions may include an agricultural machine having a tire configured to engage soil within a field. The system may also include an image capture device configured to capture one or more images of the tire as the agricultural machine is moved across the field. Furthermore, the system may include a controller communicatively coupled to the image capture device. As such, the controller may be configured to estimate a parameter associated with a soil condition of the soil within the field based on the one or more images captured by the image capture device.

8 Claims, 5 Drawing Sheets

(56) References Cited

U.S. PATENT DOCUMENTS

| | | |
|---|---|---|
| 7,301,445 B2 | 11/2007 | Moughler |
| 8,141,414 B2 | 3/2012 | Braghiroli |
| 8,175,819 B2 | 5/2012 | Fujisawa |
| 9,085,203 B2 | 7/2015 | Duppong et al. |
| 9,085,205 B2 | 7/2015 | Son |
| 9,649,889 B2 | 5/2017 | Engel et al. |
| 2002/0189336 A1 | 12/2002 | McEwan |
| 2007/0296568 A1 | 12/2007 | Uehara |
| 2013/0046419 A1* | 2/2013 | Anderson ............ E02F 9/2054 701/2 |
| 2014/0303854 A1* | 10/2014 | Zielke ................ A01B 63/008 701/50 |
| 2017/0368892 A1 | 12/2017 | Heuermann et al. |
| 2018/0092295 A1* | 4/2018 | Sugumaran .......... G05D 1/0246 |
| 2018/0184581 A1* | 7/2018 | Morgan ............... A01C 21/007 |
| 2019/0075710 A1* | 3/2019 | Strnad .................. A01B 76/00 |
| 2019/0195788 A1* | 6/2019 | Liu ................. G05B 19/41845 |
| 2020/0128723 A1* | 4/2020 | Eichhorn ............... G01N 33/24 |

\* cited by examiner

SYSTEM FOR ESTIMATING FIELD CONDITIONS AND ASSOCIATED METHODS FOR ADJUSTING OPERATING PARAMETERS OF AN AGRICULTURAL MACHINE BASED ON ESTIMATED FIELD CONDITIONS

FIELD

The present disclosure generally relates to agricultural machines and, more particularly, to systems for estimating field conditions encountered by an agricultural machine and associated methods for adjusting operating parameters of the agricultural machine based on estimated field conditions.

BACKGROUND

Agricultural machines, such as agricultural vehicles or implements, may travel across a field to perform an agricultural operation (e.g., tilling, planting, harvesting, etc.) thereon. As such, an agricultural vehicle typically includes an engine and a transmission coupled to the engine. The transmission may transfer power generated by the engine to a plurality of wheels or tires mounted on the agricultural vehicle. When driven by the engine, the tires move the agricultural vehicle across the field. However, when the field is wet or muddy, the tires may lose traction with the ground. Such a loss of traction may reduce the speed at which the agricultural vehicle is moved across the field and/or result in the vehicle getting stuck within the field. Furthermore, it may be difficult for the agricultural vehicle operator to identify wet and/or muddy conditions within the field until a loss of traction occurs.

Accordingly, an improved system for estimating field conditions and associated method for adjusting operating parameters of an agricultural machine based on estimated field conditions would be welcomed in the technology.

BRIEF DESCRIPTION

Aspects and advantages of the technology will be set forth in part in the following description, or may be obvious from the description, or may be learned through practice of the technology.

In one aspect, the present subject matter is directed to a system for estimating field conditions. The system may include an agricultural machine having a tire configured to engage soil within a field. The system may also include an image capture device configured to capture one or more images of the tire as the agricultural machine is moved across the field. Furthermore, the system may include a controller communicatively coupled to the image capture device. As such, the controller may be configured to estimate a parameter associated with a soil condition of the soil within the field based on the one or more images captured by the image capture device.

In another aspect, the present subject matter is directed to a method for adjusting operating parameters of an agricultural machine based on estimated field conditions. The agricultural machine may include a tire configured to engage soil within a field. The method may include receiving, with a computing device, one or more images of a tread portion of the tire as the agricultural machine is moved across the field. The method may also include analyzing, with the computing device, the one or more images to detect soil carried by the tread portion of the tire. Furthermore, the method may include estimating, with the computing device, a parameter associated with a soil condition of the soil within the field based on the one or more images of the soil carried by the tread portion of the tire. Additionally, the method may include initiating, with the computing device, a control action associated with adjusting an operating parameter of the agricultural machine based on the estimated parameter.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Figure 1:
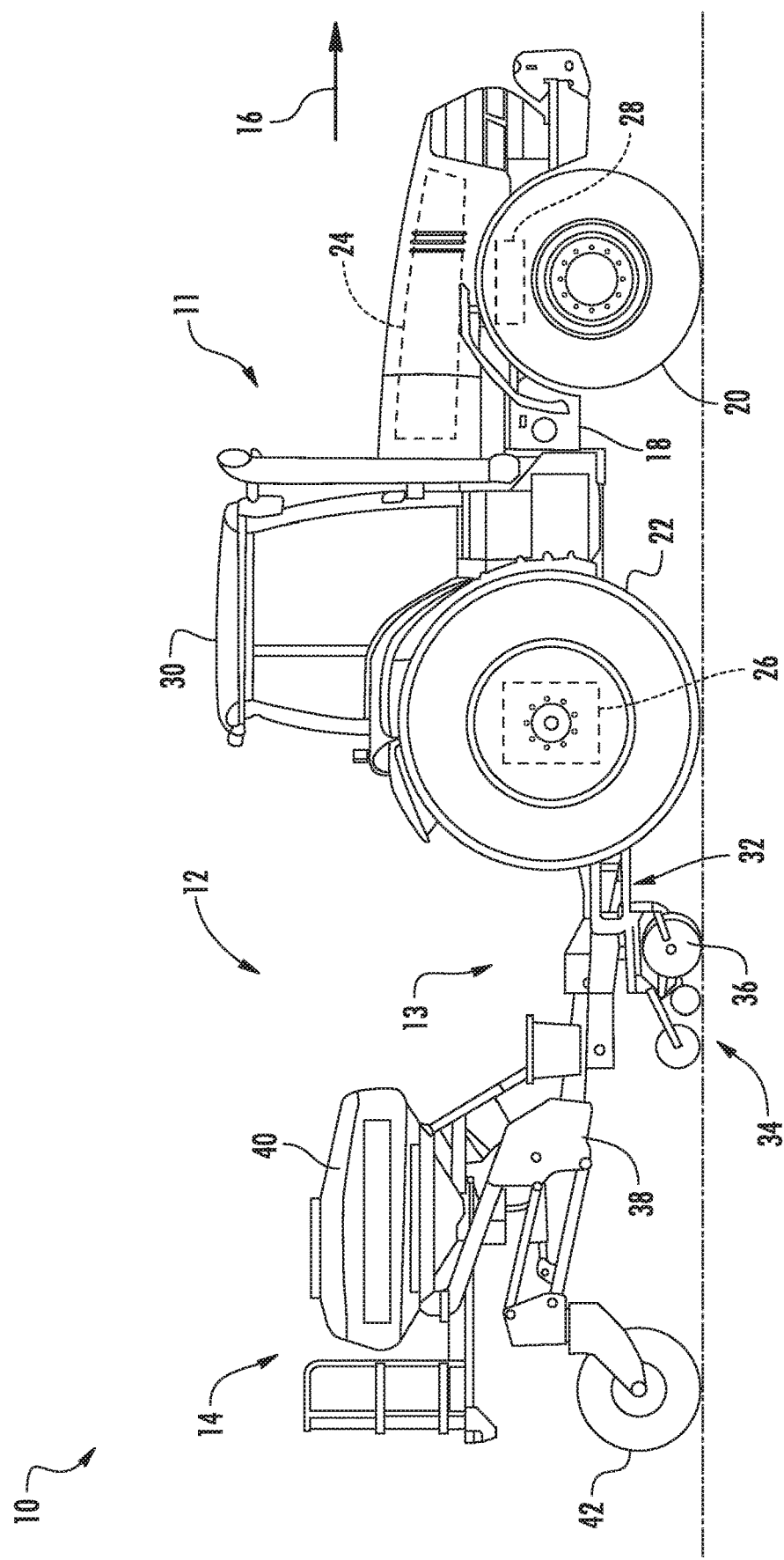
FIG. 1 illustrates a side view of one embodiment of an agricultural machine in accordance with aspects of the present subject matter, particularly illustrating the agricultural machine including an agricultural vehicle and an associated implement.

Repeat use of reference characters in the present specification and drawings is intended to represent the same or analogous features or elements of the present technology.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems for estimating field conditions and associated methods for adjusting operating parameters of an agricultural machine based on estimated field conditions. Specifically, in several embodiments, a controller of the disclosed system may be configured to receive one or more images of a tire of the agricultural machine as the machine is moved across the field. For example, in one embodiment, the received images may be indicative of the amount of soil present on the tire and/or the temperature of the tire. As such, the controller may be configured to analyze the received images to estimate a parameter associated with a soil condition of the soil within the field, such as the moisture content of the soil. Thereafter, the controller may further be configured to initiate a control action associated with adjusting an operating parameter of the agricultural machine based on the estimated parameter. For instance, the controller may be configured to adjust the travel path of, the speed of, and/or the position(s) of a ground engaging tool(s) mounted on the agricultural machine.

Referring now to the drawings, FIG. 1 illustrates a side view of one embodiment of an agricultural machine 10 in accordance with aspects of the present subject matter. As shown, in the illustrated embodiment, the agricultural machine 10 includes as an agricultural vehicle 11 and an associated agricultural implement 12. In general, the agricultural vehicle 11 may be configured to tow the implement 12 across a field in a direction of travel (e.g., as indicated by arrow 16 in FIG. 1). As shown, the agricultural vehicle 11 may be configured as an agricultural tractor and the implement 12 may be configured as a seed planting implement, such as the illustrated seed disc drill 13, and associated air cart 14. However, in other embodiments, the agricultural vehicle 11 may be configured as any other suitable type of vehicle, such as an agricultural harvester, a self-propelled sprayer, and/or the like. Similarly, in alternative embodiments, the implement 12 may be configured as any other suitable type of implement, such as seed hoe drill or another seed dispensing implement, a side dresser or another fertilizer dispensing implement, a strip tiller, a cultivator or another tillage implement, and/or the like. Furthermore, it should be appreciated that the agricultural machine 10 may correspond to any suitable powered and/or unpowered agricultural machine (including suitable vehicles and/or equipment, such as only an agricultural vehicle or only an implement). Additionally, the agricultural machine 10 may include two machines (e.g., a tractor and associated implement) more than three machines.

As shown in FIG. 1, the agricultural vehicle 11 may include a frame or chassis 18 configured to support or couple to a plurality of components. For example, a pair of steerable front tires 20 and a pair of driven rear tires 22 may be coupled to the frame 18. The tires 20, 22 may be configured to support the agricultural vehicle 11 relative to the ground and move the vehicle 11 in the direction of travel 16 across the field. In this regard, the agricultural vehicle 11 may include an engine 24 and a transmission 26 mounted on the frame 18. The transmission 26 may be operably coupled to the engine 24 and may provide variably adjusted gear ratios for transferring engine power to the driven tires 22. Furthermore, the agricultural vehicle 11 may include a steering actuator 28 configured to adjust the orientation of the steerable wheels 20 relative to the frame 18. For example, the steering actuator 28 may correspond to an electric motor, a linear actuator, a hydraulic cylinder, a pneumatic cylinder, or any other suitable actuator coupled to suitable mechanical assembly, such as a rack and pinion or a worm gear assembly. Additionally, an operator's cab 30 may be supported by a portion of the frame 18 and may house various input devices (e.g., a user interface 102 shown in FIG. 3) for permitting an operator to control the operation of one or more components of the agricultural machine 10. However, it should be appreciated that, in alternative embodiments, the agricultural vehicle 11 may have any other suitable configuration. For example, in one alternative embodiment, the front tires 20 may be driven in addition to or in lieu of the rear tires 22. In another alternative embodiment, the frame 18 may be articulated in addition to or in lieu of the steerable tires 20.

As shown, the seed disc drill 13 may be configured to be towed directly behind the agricultural vehicle 11, with the air cart 14 being towed behind the seed disc drill 13. In this regard, a hitch assembly (not shown) may be configured to couple the seed disc drill 13 to the agricultural vehicle 11. Furthermore, another hitch assembly (not shown) may be configured to couple the air cart 14 to the seed disc drill 13. However, in an alternative embodiment, the air cart 14 may be towed directly behind the agricultural vehicle 11, with the seed disc drill 13 being towed behind the air cart 14. In a further embodiment, the seed disc drill 13 and the air cart 14 may be part of a single unit that is towed behind the agricultural vehicle 11.

In several embodiments, the seed disc drill 13 may include a toolbar 32 configured to support or couple to various components of the seed disc drill 13, such as one or more row units 34. Each row unit 34 may include one or more ground engaging tools, such as the illustrated disc openers 36, configured to excavate a furrow or trench in soil to facilitate deposition of a flowable granular or particulate-type agricultural product, such as seeds, fertilizer, and/or the like. It should be appreciated that the seed disc drill 13 may generally include any number of row units 34 to facilitate delivery of the agricultural product across a given swath of the soil. For instance, in one embodiment, the seed disc drill 13 may include twenty-four row units 34 spaced apart across the width of the seed disc drill 13. In alternative embodiments, however, the seed disc drill 13 may include any other suitable number of row units 34, such as less than twenty-four row units 34 or more than twenty-four row units 34. Moreover, it should be appreciated that, in alternative embodiments, the ground engaging tool(s) may be configured as a hoe(s), a coulter(s), a shank(s), or any suitable tool(s).

Furthermore, the air cart 14 may be configured to store a flowable granular or particulate-type agricultural product, such as seeds, fertilizer, and/or the like, to be deposited within the soil. Specifically, in several embodiments, the air cart 14 may include a frame 38 configured to support or couple to various components of the air cart 14. For example, as shown, the frame 38 may be configured to support a hopper or storage tank 40 configured for storing the agricultural product to be deposited within the furrow. Furthermore, in one embodiment, a plurality of wheels or tires 42 may be coupled to the frame 38 to permit the air cart 14 to be towed across a field by the agricultural vehicle 11.

Figure 2:
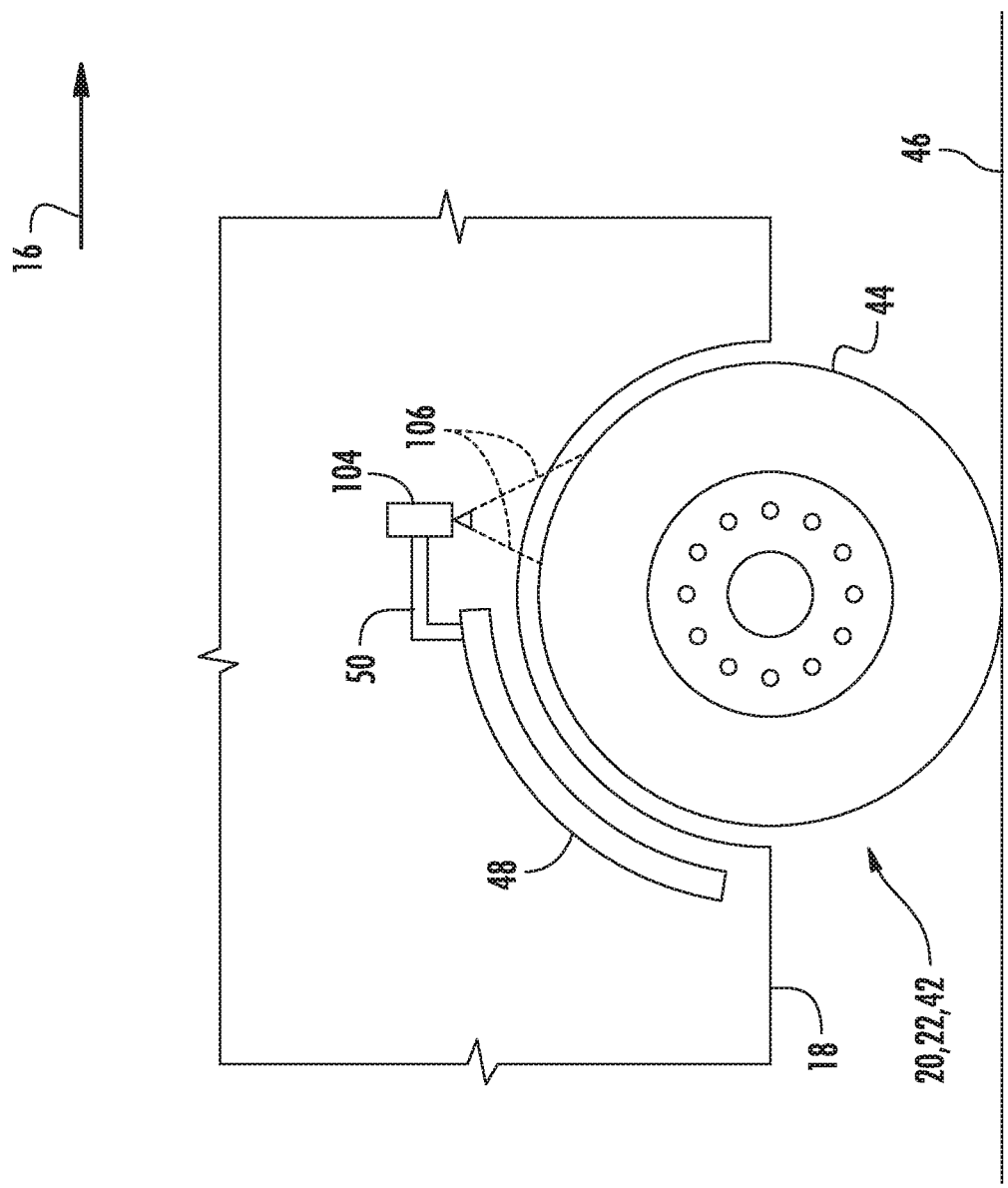
FIG. 2 illustrates an enlarged side view of the agricultural machine shown in FIG. 1, particularly illustrating an image capture device mounted on the machine in accordance with aspects of the present subject matter.

Referring now to FIG. 2, an enlarged side view of a portion of the agricultural machine 10 is illustrated in accordance with aspects of the present subject matter. As indicated above, the tires 20, 22, 42 of the agricultural machine 10 may be configured to move the machine 10 across the field. In this regard, each of the tires 20, 22, 42 may include a tread portion 44 configured to engage or otherwise contact the soil 46 within the field as the agricultural machine 10 is moved in the direction of travel 16. As shown, in several embodiments, the tread portion 44 of the tires 20, 22, 42 may generally correspond to the circumferentially outer surface of the tires 20, 22, 42. It should be appreciated that the tread portion 44 may have any suitable pattern or configuration to facilitate movement of the agricultural machine 10 across the field.

In accordance with aspects of the present subject matter, the agricultural machine 10 may include an image capture device 104 coupled thereto and/or supported thereon. Specifically, in several embodiments, the image capture device 104 may be configured to capture one or more images of a portion of one of the tires 20, 22, 42 as the agricultural machine 10 travels across the field. As will be described below, the images captured by the image capture device 104 may then be used to estimate a soil condition parameter, such as a soil moisture parameter, of the soil 46 across which the agricultural machine 10 is traveling. In one embodiment, the image capture device 104 may be configured to continuously capture images of the tire 20, 22, 42 as the agricultural machine 10 travels across the field. However, in an alternative embodiment, the image capture device 104 may be configured to capture images of the tire 20, 22, 42 at a predetermined time interval (e.g., every one second, every five seconds, every ten seconds, etc.) as the agricultural machine 10 travels across the field.

As shown in FIG. 2, the image capture device 104 may be installed on or otherwise provided in operative association with the agricultural machine 10 such that the image capture device 104 has a field of view or sensor detection range (e.g., as indicated by dashed lines 106 in FIG. 2) directed towards a portion of one of the tires 20, 22, 42. For example, in one embodiment, the image capture device 104 may be installed or otherwise positioned on a fender 48 of the agricultural vehicle 11, such as via a suitable mounting arm 50. As such, the image capture device 104 may be able to capture images of the tread portion 44 of the corresponding tire 20, 22, 42. However, it should be appreciated that, in alternative embodiments, the image capture device 104 may be positioned on and/or coupled to the any other suitable component of or location on the agricultural machine 10, such as a frame member of the implement 12. Furthermore, although FIG. 2 shows one image capture device 104, it should further be appreciated that the agricultural machine 10 may include additional image capture devices 104 such that images of more than one of the tires 20, 22, 42 are captured.

Moreover, it should be appreciated that the image capture device 104 may correspond to any suitable device(s) configured to detect or capture image data associated with the tire 20, 22, 42 present within an associated field of view. For example, in several embodiments, the image capture device 104 may correspond to a suitable camera(s) configured to capture images of the tread portion 44 of the tire 20, 22, 42, such as three-dimensional images of the tread portion 44 present with in the associated field of view. For instance, in a particular embodiment, the vision-based sensor(s) 104 may correspond to a stereographic camera(s) having two or more lenses with a separate image sensor for each lens to allow the camera(s) to capture stereographic or three-dimensional images. As will be described below, such three-dimensional images may provide an indication of the amount and/or thickness of soil present on the thread portion 44 of the tire 20, 22, 42. In another embodiment, the image capture device 104 may correspond to a suitable infrared camera(s) configured to capture infrared images of the tread portion 44 of the tire 20, 22, 42 present with in the associated field of view. As will be described below, such infrared images may be indicative of the temperature of the soil present on the thread portion 44 of the tire 20, 22, 42. However, in alternative embodiments, the image capture device 104 may correspond to any other suitable image capturing device(s).

Additionally, it should be further appreciated that the configurations of the agricultural machine 10 described above and shown in FIGS. 1 and 2 is provided only to place the present subject matter in an exemplary field of use. Thus, it should be appreciated that the present subject matter may be readily adaptable to any manner of machine configuration.

Figure 3:
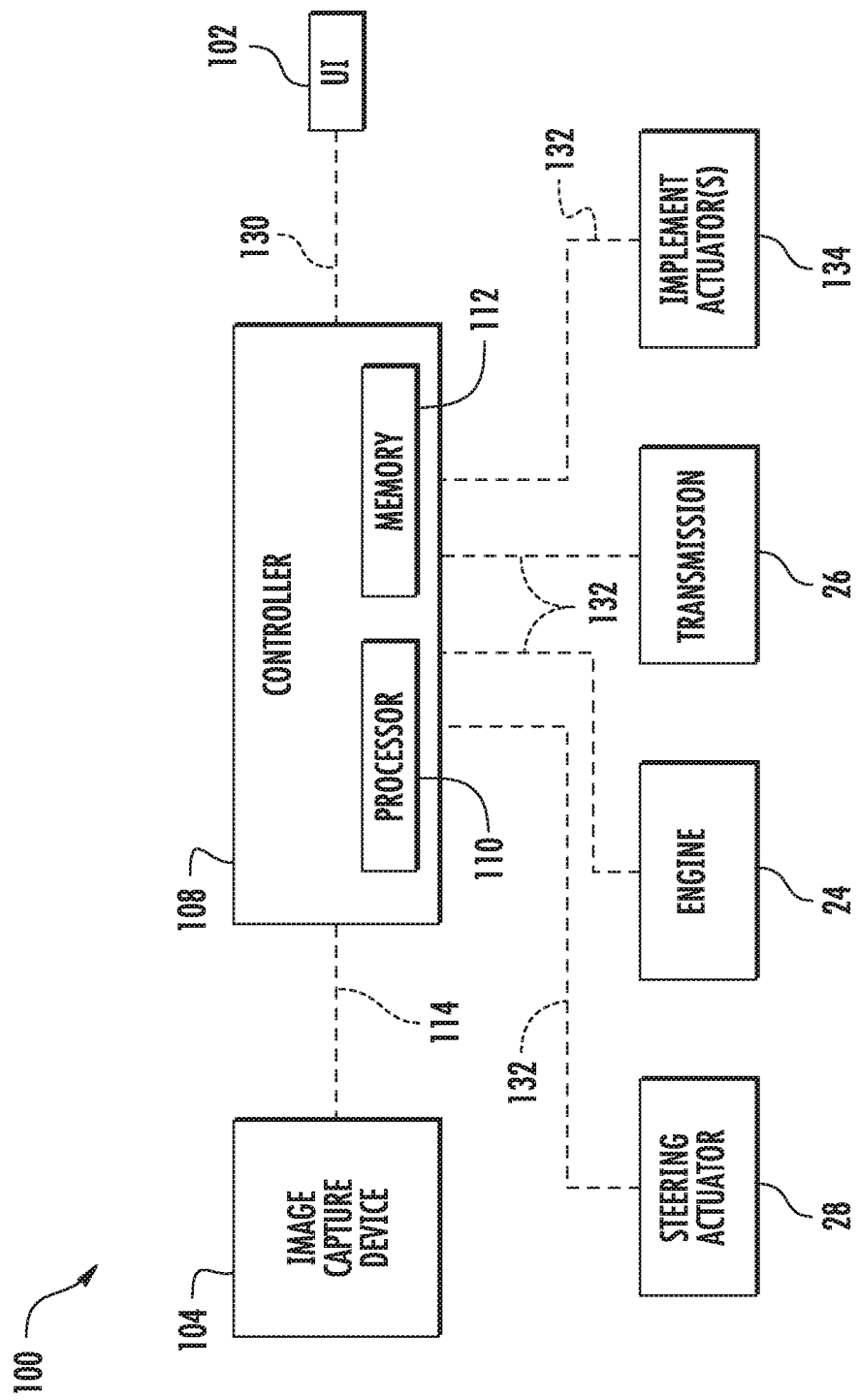
FIG. 3 illustrates an schematic view of one embodiment of a system for estimating field conditions in accordance with aspects of the present subject matter.

Referring now to FIG. 3, a schematic view of one embodiment of a system 100 for estimating field conditions is illustrated in accordance with aspects of the present subject matter. In general, the system 100 will be described herein with reference to the agricultural machine 10 described above with reference to FIGS. 1 and 2. However, it should be appreciated by those of ordinary skill in the art that the disclosed system 100 may generally be utilized with agricultural machines having any other suitable machine configuration.

As shown, the system 100 may include a controller 108 configured to electronically control the operation of one or more components of the agricultural machine 10. In general, the controller 108 may comprise any suitable processor-based device known in the art, such as a computing device or any suitable combination of computing devices. Thus, in several embodiments, the controller 108 may include one or more processor(s) 110 and associated memory device(s) 112 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 112 of the controller 108 may generally comprise memory element(s) including, but not limited to, a computer readable medium (e.g., random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 112 may generally be configured to store suitable computer-readable instructions that, when implemented by the processor(s) 110, configure the controller 108 to perform various computer-implemented functions, such as one or more aspects of the method 200 described below with reference to FIG. 5. In addition, the controller 108 may also include various other suitable components, such as a communications circuit or module, one or more input/output channels, a data/control bus and/or the like.

It should be appreciated that the controller 108 may correspond to an existing controller of the agricultural machine 10 or the controller 108 may correspond to a separate processing device. For instance, in one embodiment, the controller 108 may form all or part of a separate plug-in module that may be installed within the agricultural machine 10 to allow for the disclosed system and method to be implemented without requiring additional software to be uploaded onto existing control devices of the agricultural machine 10.

Furthermore, in one embodiment, the system 100 may also include a user interface 102. More specifically, the user interface 102 may be configured to provide feedback (e.g., information associated with the estimated soil condition parameter) to the operator of the agricultural machine 10. As such, the user interface 102 may include one or more feedback devices (not shown), such as display screens, speakers, warning lights, and/or the like, which are configured to communicate such feedback. In addition, some embodiments of the user interface 102 may include one or more input devices (not shown), such as touchscreens, keypads, touchpads, knobs, buttons, sliders, switches, mice, microphones, and/or the like, which are configured to receive user inputs from the operator. In one embodiment, the user interface 102 may be positioned within the cab 30 of the agricultural vehicle 11. However, in alternative embodiments, the user interface 102 may have any suitable configuration and/or be positioned in any other suitable location on the agricultural machine 10.

In several embodiments, the controller 108 may be configured to receive one or more images of the tire 20, 22, 42 as the agricultural machine 10 travels across the field. Specifically, as shown in FIG. 3, the controller 108 may be communicatively coupled to the image capture device 104 via a wired or wireless connection to allow image data (e.g., indicated by dashed line 114 in FIG. 3) to be transmitted from the image capture device 104 to the controller 108. For example, in one embodiment, the controller 108 may be configured to continuously receive images via the image data 114 as the agricultural machine 10 travels across the field. However, in an alternative embodiment, the controller 108 may be configured to receive images via the image data 114 at a predetermined sampling rate or time interval as the agricultural machine 10 travels across the field.

The controller 108 may be configured to estimate a soil condition parameter(s) of the soil within the field based on the received image(s). More specifically, as the agricultural machine 10 travels across the field, one or more characteristics of the tires 20, 22, 42, such as the amount and/or temperature of the soil present on the tread portions 44 thereof, may be correlated or otherwise associated with the soil conditions present within the field. Moreover, the received image(s) may be indicative of such characteristic(s) of the portion of the tire 20, 22, 42 present within the field of view 106 of the image capture device 104. In this regard, the controller 108 may be configured to analyze the received images and estimate the soil condition parameter(s) based on the characteristics of the tire 20, 22, 42 shown in the image(s). For example, the controller 108 may include any suitable image processing algorithms stored within its memory 112 or may otherwise use any suitable image processing techniques to estimate the soil condition parameter(s) based on the tire characteristic(s) shown within the received images.

In several embodiments, the controller 108 may be configured to estimate a soil moisture parameter of the soil within the field based on the amount of soil, moisture, or other substances (e.g., fertilizer or other chemicals) present on the tires 20, 22, 42. More specifically, when the field has a high moisture content (e.g., when the field is "muddy"), soil, moisture, and/or other substances may become adhered to the tread portions 44 of the tires 20, 22, 42 as the agricultural machine 10 travels across the field. Conversely, when the agricultural machine 10 travels across a field having a low moisture content (e.g., when the field is dry), little or no soil and/or moisture may be present on the tires 20, 22, 42. As such, the amount of soil and/or moisture present on the tires 20, 22, 42 may generally be indicative of or otherwise associated with the soil moisture content within the field across which the agricultural machine 10 is traveling. Thus, the received image(s) may be provide an indication of the amount of soil and/or moisture present on the tire 20, 22, 42 present within the field of view of the image capture device 104. In this regard, the controller 108 may be configured to analyze the received image(s) to estimate the soil moisture parameter based on the amount of soil and/or moisture present on the tire 20, 22, 42. For example, the controller 108 may be configured to estimate the soil moisture parameter based on the thickness of the soil present on the tire 20, 22, 42 and/or the percentage of the tread portion 44 of the tire 20, 22, 42 on which soil is present.

Figure 4:
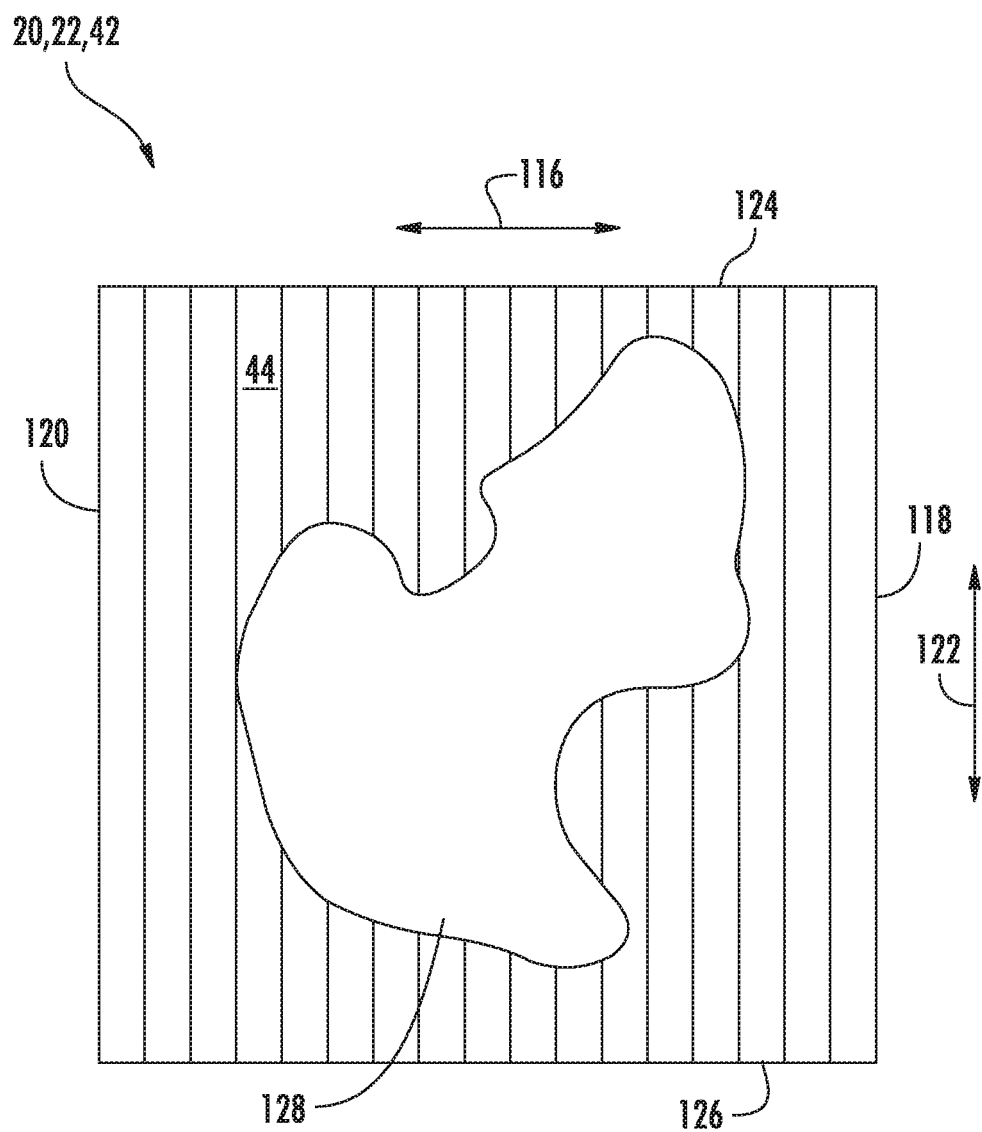
FIG. 4 illustrates an example image of a portion of a tire of an agricultural machine in accordance with aspects of the present subject matter, particularly illustrating soil present on a tread portion of the tire.

Referring now to FIG. 4, an example image of a section of one of the tires 20, 22, 42 is illustrated in accordance with aspects of the present subject matter. In general, the example image corresponds to a section of the tread portion 44 of the tire 20, 22, 42 extending along a lateral direction (e.g., as indicated by arrow 116 in FIG. 4) between an inner side wall 118 and an outer sidewall 120 of the tire 20, 22, 42. Furthermore, the section of the tread portion 44 shown in the example image extends along a circumferential direction (e.g., as indicated by arrow 122 in FIG. 4) between a first circumferential boundary or edge 124 and a second circumferential boundary or edge 126. In the example shown, soil 128 is present on approximately fifty percent of the section of the tire 20, 22, 42 visible within the example image. In such instance, the controller 108 may analyze the example image to determine such percentage and, thereafter, estimate a soil moisture parameter of the soil present within the field based on the determined percentage. It should be appreciated that the first and second circumferential boundaries 124, 126 are generally based on the field of view of the image capture device 104. As such, if the image capture device 104 is mounted in such a manner that provides a larger field of view, the first and second circumferential boundaries 124, 126 may be spaced farther apart along the circumferential direction 122. Furthermore, although the entire lateral width of the tire 20, 22, 42 (i.e., from the inner sidewall 118 to the outer sidewall 120) is shown in the example image, it should be appreciated that images captured by the image capture device 104 may show only a portion of the lateral width of the tire 20, 22, 42.

Additionally, in one embodiment, the controller 108 may be configured to estimate the soil moisture parameter of the soil within the field based on the temperature of the soil present on the tires 20, 22, 42. More specifically, when the agricultural machine 10 travels across the field, the temperature of the soil present on the tread portions 44 of the tires 20, 22, 42 may have a lower temperature when the field has a high moisture content (e.g., when the field is "muddy") than when the field has a low moisture content (e.g., when the field is dry). As indicated above, the received image(s) may be indicative of the temperature of the tire 20, 22, 42 present within the field of view of the image capture device 104, such as when the image capture device 104 corresponds to an infrared camera. In this regard, the controller 108 may be configured to analyze the received image(s) to determine the temperature of the tread portion 44 of the tire 20, 22, 42. Thereafter, the controller 108 may be configured to estimate the soil moisture parameter based on the determined temperature of the tire 20, 22, 42. However, it should be appreciated that, in alternative embodiments, the controller 108 may be configured to estimate the soil moisture parameter based on any other characteristic or parameter associated with the image(s) of the tire 20, 22, 42.

Referring back to FIG. 3, in one embodiment, the controller 108 may be configured to initiate a display of the estimated soil condition parameter to the operator of the agricultural machine 10. Specifically, as shown, the controller 108 may be communicatively coupled to the user interface 102 via a wired or wireless connection to allow feedback signals (e.g., indicated by dashed line 130 in FIG. 3) to be transmitted from the controller 108 to the user interface 102. Based on such feedback signals 130, the user interface 102 may be configured to display the value associated with the estimated soil condition parameter to the machine operator. For example, in embodiments in which the controller 108 continuously receives images from the image capture device 104, the value displayed by the user interface 102 may be continuously updated in real time as the agricultural machine 10 travels across the field. It should be appreciated that the operator may be a human or an autonomous vehicle control system.

In accordance with aspects of the present subject matter, the controller 108 may further be configured to initiate a control action associated with adjusting one or more operating parameters of the agricultural machine 10 when it is determined that the estimated soil condition parameter has fallen outside a predetermined soil condition parameter range. Specifically, in several embodiments, the controller 108 may be configured to compare the estimated soil condition parameter to a predetermined soil condition parameter range. Thereafter, in the event that the estimated soil condition parameter exceeds a maximum soil condition parameter threshold for the given soil condition parameter range or falls below a minimum soil condition parameter threshold for such range (thereby indicating that the soil condition parameter of the soil within the field may be too high or too low), the controller 108 may be configured to initiate a control action associated with adjusting an operating parameter of the agricultural machine 10.

In one embodiment, the controller 108 may be configured to notify the operator of the agricultural machine 10 that the estimated soil condition parameter has fallen outside of the predetermined operating distance range. In such embodiment, the controller 108 may be configured to transmit feedback signals 130 to the user interface 102 instructing the user interface 102 to provide a notification to the operator of the agricultural machine 10 (e.g., by causing a visual or audible notification or indicator to be presented to the operator within the cab 30 of the agricultural vehicle 11) that provides an indication that the estimated soil condition parameter has fallen outside of the predetermined soil condition parameter range. In such instances, the operator may then choose to initiate any suitable corrective action he/she believes is necessary, such as by adjusting the travel path and/or speed of the agricultural vehicle 11 and/or adjusting the position(s) of the ground engaging tool(s) of the implement 12.

Moreover, in several embodiments, the controller 108 may be configured to automatically adjust one or more operating parameters of the agricultural machine 10 when it is determined that the estimated soil condition parameter has fallen outside the predetermined soil condition parameter range. Specifically, as shown in FIG. 3, the controller 108 may be communicatively coupled to one or more components of the agricultural machine 10, such as the engine 24, the transmission 26, and/or the steering actuator 28, via a wired or wireless connection to allow control signals (e.g., indicated by dashed lines 132 in FIG. 3) to be transmitted from the controller 108 to such components 24, 26, 28. As such, the controller 108 may be configured to transmit control signals 132 to the engine 24, the transmission 26, and/or the steering actuator 28 instructing such components 24, 26, 28 to adjust the direction of travel 16, travel path, and/or speed of the agricultural machine 10. For example, the control signals 132 may instruct the engine 24 to increase or decrease its power output to increase or decrease the speed at which the agricultural vehicle 11 is moved across the field. Similarly, the control signals 132 may instruct the transmission 26 to upshift or downshift to increase or decrease the speed at which the agricultural vehicle 11 is moved across the field. Moreover, the control signals 132 may instruct the steering actuator 28 to adjust the direction of travel 16 and/or travel path of the agricultural vehicle 11 across the field.

Additionally, in several embodiments, the controller 108 may be configured to automatically adjust one or more operating parameters of the implement 12 when it is determined that the estimated soil condition parameter has fallen outside the predetermined soil condition parameter range. Specifically, as shown in FIG. 3, the controller 108 may be communicatively coupled to one or more implement actuators 134 via a wired or wireless connection to allow control signals 132 to be transmitted from the controller 108 to the implement actuator(s) 134. In general, the implement actuator(s) 134 may correspond to any suitable device(s) on the agricultural machine 10 that is configured to adjust the operating parameter(s) of the implement 12. For example, in one embodiment, the implement actuator(s) 134 may correspond to a valve(s) configured to control the operation of one or more fluid-driven cylinders (not shown) on the implement 12, with such cylinder(s) being configured to control the position of one or more ground engaging tools, such the disc openers 36, of the implement 12 relative to the ground. As such, the controller 108 may be configured to transmit control signals 132 to the implement actuator(s) 134 instructing such implement actuator(s) 134 to adjust the position of the ground engaging tool(s) of the implement 12 relative to the ground, such by raising or lowering the ground engaging tool(s).

As indicated above, the soil condition parameter may be indicative of the moisture content of the soil within the field. In such embodiments, the controller 108 may be configured to compare the values associated with the estimated soil moisture parameter to a predetermined maximum soil moisture threshold defined for the agricultural machine 10. Thereafter, in the event that the estimated soil moisture parameter exceeds the maximum soil moisture parameter threshold (thereby indicating that the moisture content of the soil within the field may be too high), the controller 108 may be configured to initiate a control action associated with adjusting an operating parameter of the agricultural machine 10. For example, in one embodiment, the controller 108 may be configured to notify the operator of agricultural machine 10 that the estimated soil moisture parameter has exceeded the maximum soil moisture parameter threshold. In such instances, the operator may then choose to initiate any suitable corrective action he/she believes is necessary, such as by adjusting the travel path of the agricultural vehicle 11, increasing the speed of the agricultural vehicle 11, and/or lifting the ground engaging tool(s) of the implement 12 out of the ground.

Moreover, in several embodiments, the controller 108 may be configured to automatically adjust one or more operating parameters of the agricultural machine 10 when it is determined that the estimated soil moisture parameter has exceeded the maximum soil moisture parameter threshold. For example, when the agricultural machine 10 encounters a portion of the field in which the maximum soil moisture parameter threshold has been exceeded (e.g., a "muddy" portion of the field), it may be desirable to adjust the travel path of the machine 10 to prevent the machine 10 from getting stuck within the field. As such, in one embodiment, the controller 108 may be configured to transmit control signals 132 to the steering actuator 28 instructing the steering actuator 28 to adjust the direction of travel 16 of the agricultural machine 10 such that the travel path of the machine 10 is directed to a dryer portion of the field.

Furthermore, it may be desirable to increase the speed of the agricultural machine 10 when the machine 10 encounters a portion of the field in which the maximum soil moisture parameter threshold has been exceeded to prevent the machine 10 from getting stuck within the field. In this regard, the controller 108 may be configured to transmit control signals 132 to the engine 24 instructing the engine 24 to increase its power output to increase the speed at which the agricultural vehicle 11 travels across the field. Similarly, the controller 108 may be configured to transmit control signals 132 to the transmission 26 instructing the transmission 26 to upshift to increase the speed at which the agricultural vehicle 11 travels across the field.

Moreover, in several embodiments, the controller 108 may be configured to automatically adjust one or more operating parameters of the implement 12 when it is determined that the estimated soil moisture parameter has exceeded the maximum soil moisture parameter threshold. For example, when the agricultural machine 10 encounters a portion of the field in which the maximum soil moisture parameter threshold has been exceeded, it may be desirable to decrease the penetration depth of the ground engaging tool(s) on the implement 12 to reduce the draft load on the agricultural vehicle 11 in a manner that prevents the machine 10 from getting stuck within the field. As such, in one embodiment, the controller 108 may be configured to transmit control signals 132 to the implement actuator(s) 134 instructing the implement actuator(s) 134 to decrease the penetration depth of the disc openers 36. Moreover, it may be desirable to lift the ground engaging tool(s) on the implement 12 entirely out of the ground, such as to a non-operational position, when the agricultural machine 10 encounters a portion of the field in which the maximum soil moisture parameter threshold has been exceeded to prevent the machine 10 from getting stuck within the field. In this regard, in one embodiment, the controller 108 may be configured to transmit control signals 132 to the implement actuator(s) 134 instructing the implement actuator(s) 134 to raise the disc openers 36 such that the disc openers 36 lifted out of the soil.

Additionally, the controller 108 may be configured to control the penetration depth(s) of the ground engaging tool(s) mounted on the implement 12 based on the estimated soil moisture parameter. Specifically, in one embodiment, the controller 108 may be configured to control the penetration depths of the disc openers 36 based on the estimated soil moisture parameter. In general, it may be desirable that the planting depth of seeds within the field be shallower when the soil moisture content is high and deeper when the soil moisture content is low. As such, the controller 108 may be configured to transmit control signals 132 to the implement actuator(s) 134 instructing the implement actuator(s) 134 to vary the penetration depths of the disc openers 36 based on the estimated soil moisture parameter. For example, when the estimated soil moisture parameter increases, the control signals 132 may instruct the implement actuator(s) 134 to reduce the penetration depths of the disc openers 36. Conversely, when the estimated soil moisture parameter decreases, the control signals 132 may instruct the implement actuator(s) 134 to increase the penetration depths of the disc openers 36. However, it should be appreciated that, in alternative embodiments, the controller 108 may be configured to control any other suitable parameter(s) of any other suitable implement components based on the estimated soil moisture parameter. For example, in an embodiment in which the ground engaging tool(s) are configured as harrow tines, the controller 108 may be configured to control the down pressure loads applied to such tines based on the estimated soil moisture parameter, such as by decreasing the down pressure loads when the soil moisture parameter increases and increasing the down pressure loads when the soil moisture parameter decreases.

Figure 5:
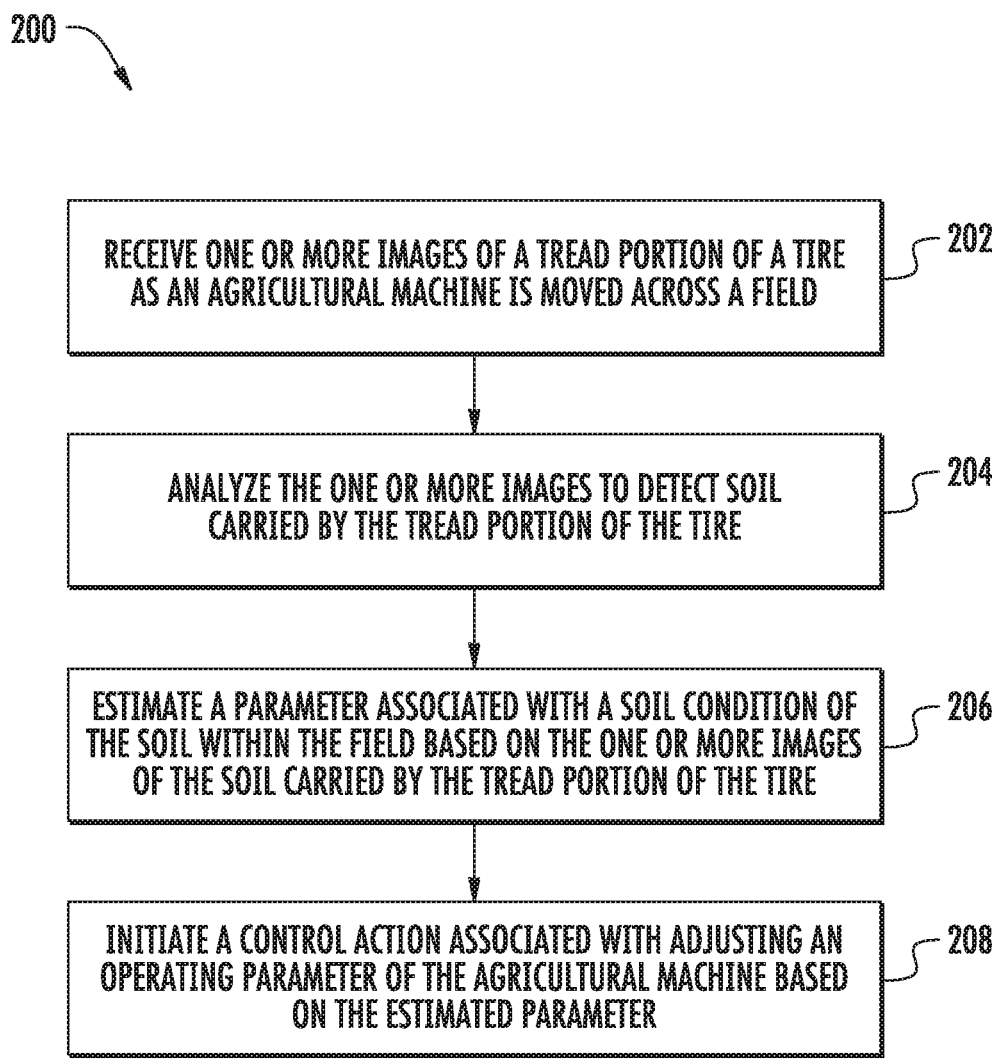
FIG. 5 illustrates a flow diagram of one embodiment of a method for adjusting operating parameters of an agricultural machine in accordance with aspects of the present subject matter.

Referring now to FIG. 5, a flow diagram of one embodiment of a method 200 for adjusting operating parameters of an agricultural machine based on estimated field conditions is illustrated in accordance with aspects of the present subject matter. In general, the method 200 will be described herein with reference to the agricultural machine 10 and the system 100 described above with reference to FIGS. 1-4. However, it should be appreciated by those of ordinary skill in the art that the disclosed method 200 may generally be utilized to adjust operating parameters of any agricultural machine any suitable machine configuration and/or in connection with any system having any suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving, with a computing device, one or more images of a tread portion of a tire as an agricultural machine is moved across a field. For instance, as indicated above, the controller 108 may be communicatively coupled to the image capture device 104, which is configured to capture one or more images of a portion, such as the tread portion 44, of the one of the tire 20, 22, 42 as the agricultural machine 10 travels across the field. As such, the controller 108 may be configured to receive the images of the tire 20, 22, 42 from the image capture device 104.

Additionally, at (204), the method 200 may include analyzing, with the computing device, the one or more images to detect soil carried by a tread portion of the tire. For instance, as described above, the controller 108 may be configured to analyze the images received from the image capture device 104 to determine or otherwise detect soil present on the tread portion 44 of the tire 20, 22, 42, such as based on the thickness and/or temperature of the soil present on the tread portion 44 and/or the percentage of the tread portion 44 over which soil is present.

Moreover, as shown in FIG. 5, at (206), the method 200 may include estimating, with the computing device, a parameter associated with a soil condition of the soil within the field based on the one or more images of the soil carried by the tread portion of the tire. For instance, as described above, the controller 108 may be configured to estimate a soil condition parameter, such as a soil moisture parameter, of the soil within the field based on the amount of soil present on the tread portion 44 of the tire 20, 22, 42 shown in the captured images.

Furthermore, at (208), initiating, with the computing device, a control action associated with adjusting an operating parameter of the agricultural machine based on the estimated parameter. For instance, as described above, the controller 108 may be configured to transmit control signals 132 to the engine 24, the transmission 26, the steering actuator 28, and/or the implement actuator(s) 134 to adjust one or more operating parameters of the agricultural machine 10 based on the estimated soil condition parameter.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A method for adjusting operating parameters of an agricultural machine based on estimated field conditions, the agricultural machine including a tire configured to engage soil within a field, the method comprising:
   receiving, with a computing device, one or more images of a tread portion of the tire as the agricultural machine is moved across the field;
   analyzing, with the computing device, the one or more images to detect soil carried by the tread portion of the tire;
   estimating, with the computing device, an estimated parameter associated with a soil condition of the soil within the field based on the one or more images of the soil carried by the tread portion of the tire; and
   initiating, with the computing device, a control action associated with adjusting an operating parameter of the agricultural machine based on the estimated parameter.

2. The method of claim 1, wherein the estimated parameter is indicative of a moisture content of the soil within the field.

3. The method of claim 2, wherein analyzing the one or more images comprises analyzing, with the computing device, the one or more images to estimate the estimated parameter based at least one of an amount or a temperature of soil present on the tread portion of the tire.

4. The method of claim 1, further comprising:
   initiating, with the computing device, display of the estimated parameter to an operator of the agricultural machine.

5. The method of claim 1, further comprising:
   when the estimated parameter has fallen outside of a predetermined range, initiating, with the computing device, the control action.

6. The method of claim 5, wherein the control action is associated with adjusting a travel path of the agricultural machine across the field.

7. The method of claim 5, wherein the control action is associated with adjusting a speed of the agricultural machine relative to the field.

8. The method of claim 5, wherein the control action is associated with initiating adjustment of one or more operating parameters of an implement being towed by the agricultural machine.

* * * * *